United States Patent
Bakels et al.

(10) Patent No.: US 6,223,082 B1
(45) Date of Patent: Apr. 24, 2001

(54) FOUR-CHAMBER PACING SYSTEM FOR OPTIMIZING CARDIC OUTPUT AND DETERMINING HEART CONDITION

(75) Inventors: Arnoldus Bakels, Simpelveld; Robert Leinders, Limbricht; Cobus de Roos, Landgraaf, all of (NL)

(73) Assignee: Medtronic Inc., Minneapolis, MN (US)

( * ) Notice: Subject to any disclaimer, the term of this patent is extended or adjusted under 35 U.S.C. 154(b) by 0 days.

(21) Appl. No.: 09/493,689

(22) Filed: Jan. 28, 2000

Related U.S. Application Data (62) Division of application No. 08/990,427, filed on Dec. 15, 1997, now Pat. No. 6,070,100.

(51) Int. Cl.⁷ .................................................. A61N 1/365
(52) U.S. Cl. ................................................................ 607/17
(58) Field of Search ................................. 607/9, 11, 17, 607/24; 600/506, 507

(56) References Cited

U.S. PATENT DOCUMENTS

| | | | |
|---|---|---|---|
| 4,303,075 | 12/1981 | Heilman et al. | 128/419 PG |
| 4,928,688 | 5/1990 | Mower | 128/419 PG |
| 5,003,975 | * 4/1991 | Hafelfinger et al. | 607/28 |
| 5,058,583 | * 10/1991 | Geddes | 600/506 |
| 5,501,702 | 3/1996 | Plicchi et al. | 607/20 |
| 5,540,727 | * 7/1996 | Tockman et al. | 607/17 |

OTHER PUBLICATIONS

Daubert et al, "Simultaneous Dual Atrium Pacing in High Degree Inter–Atrial Blocks: Hemodynamic Results," *AHA* 1991, Abstract from 64th Scientific Sessions, No. 1804.

Mabo et al., "Prevention of Atrial Tachyarrythmias Related to Inter–Atrial Block By Permanent Atrial Resynchronization," *PACE*, vol. 14, No. 122, Apr. 1991, Part II, p. 648.

A. Cazeau et al., Four Chamber Pacing in Dilated Cardiomyopathy, PACE, Vo. 17, Part II, Nov. 1994, p. 1974–1979.

* cited by examiner

*Primary Examiner*—William E. Kamm
(74) *Attorney, Agent, or Firm*—Thomas F. Woods; Michael J. Jaro; Harold Patton (57) ABSTRACT

A pacing system and method for providing multiple chamber pacing of a patient's heart, and in particular, pacing programmed for treatment of various forms of heart failure. The system utilizes impedance sensing for determining optimum pacing parameters, e.g., for pacing the left ventricle so that left heart output is maximized. The impedance sensing also is used for determination of arrhythmias or progression of heart failure. Impedance sensing is provided for between selected pairs of the four chambers, to enable optimizing of information for control and diagnosis. In a preferred embodiment impedance measurements are obtained for determining the timing of right heart valve closure or right ventricular contractions, and the timing of delivery of left ventricular pace pulses is adjusted so as to optimally synchronize left ventricular pacing with the right ventricular contractions. Impedance sensing in the left heart also provides timing of mechanical contraction, and the pacemaker controls pacing to maintain bi-ventricular mechanical synchronization adjusted for maximum cardiac output.

5 Claims, 10 Drawing Sheets

FOUR-CHAMBER PACING SYSTEM FOR OPTIMIZING CARDIC OUTPUT AND DETERMINING HEART CONDITION

This divisional patent application corresponds to patent U.S. patent application Ser. No. 08/990,427 filed Dec. 15, 1997, now U.S. Pat. No. 6,070,100, for "Four-Chamber Pacing System for Optimizing Cardiac Output and Determining Heart Condition" to Leinders et al.

FIELD OF THE INVENTION

This invention relates to cardiac pacing systems and, more particularly, to four-chamber pacing systems with sensors for measuring cardiac mechanical characteristics so as to improve cardiac output for congestive heart failure and other patients.

BACKGROUND OF THE INVENTION

Congestive heart failure (CHF) is defined generally as the inability of the heart to deliver enough blood to the peripheral tissues to meet metabolic demands. Frequently CHF is manifested by left heart dysfunction, but it can have a variety of sources. For example, CHF patients may have any one of several different conduction defects. The natural electrical activation system through the heart involves sequential events starting with the sino-atrial (SA) node, and continuing through the atrial conduction pathways of Bachmann's bundle and internodal tracts at the atrial level, followed by the atrio-ventricular (AV) node, Common Bundle of His, right and left bundle branches, and final distribution to the distal myocardial terminals via the Purkinje fiber network. A common type of intra-atrial conduction defect is known as intra-atrial block (IAB), a condition where the atrial activation is delayed in getting from the right atrium to the left atrium. In left bundle branch block (LBBB) and right bundle branch block (RBBB), the activation signals are not conducted in a normal fashion along the right or left bundle branches respectively. Thus, in a patient with bundle branch block, the activation of the ventricle is slowed, and the QRS is seen to widen due to the increased time for the activation to traverse the conduction path.

CHF manifested by such conduction defects and/or other cardiomyopathies are the object of considerable research into treatments for improving cardiac output. For example, drug companies have recognized CHF as a market opportunity, and are conducting extensive clinical studies organized to test the outcome of newly developed drugs in terms of improving cardiac performance in these patients.

Likewise, it is known generally that four-chamber cardiac pacing is feasible, and can provide significant improvement for patients having left atrial-ventricular dysfunction, or other forms of cardiac heart failure. While there has been relatively little commercialization of four-chamber pacing, the hypothesis remains that cardiac pump function can clearly be improved by such pacing.

The benefits of four-chamber pacing generally have been disclosed and published in the literature. Cazeau et al., PACE, Vol. 17, November 1994, Part II, pp. 1974–1979, disclose investigations leading to the conclusion that four-chamber pacing is feasible, and that in patients with evidence of interventricular dyssynchrony, a better mechanical activation process can be obtained by resynchronizing depolarization of the right and left ventricles, and optimizing the AV sequence on both sides of the heart. In the patent literature, U.S. Pat. No. 4,928,688 is representative of a system for simultaneous left ventricular (LV) and right ventricular (RV) pacing; natural ventricular depolarizations are sensed in both chambers, if one chamber contracts but the other one does not within a window of up to 5–10 ms, then the non-contracting ventricular chamber is paced.

In addition to the above-mentioned disclosures concerning the advantages of substantially simultaneous or synchronous pacing of the two ventricles, it is known that there is an advantage to synchronous pacing of the left atrium and the right atrium for patients with IAB, inter-atrial block. In a normal heart, atrial activation initiates with the SA node, located in the right atrial wall. In a patient with IAB, the activation is slow being transferred over to the left atrium, and as a result the left atrium may be triggered to contract up to 90 ms later than the right atrium. It can be seen that if contractions in the left ventricle and the right ventricle are about the same time, then left AV synchrony is way off, with the left ventricle not having adequate time to fill up. The advantage of synchronous pacing of the two atria for patients with IAB is disclosed at AHA 1991, Abstract from 64th Scientific Sessions, "Simultaneous Dual Atrium Pacing in High Degree Inter-Atrial Blocks: Hemodynamic Results," Daubert et al., No. 1804.

Further, it is known that patients with IAB are susceptible to retrograde activation of the left atrium, with resulting atrial tachycardia. Atrial resynchronization through pacing of the atria can be effective in treating the situation. PACE, Vol. 14, April 1991, Part II, p. 648, "Prevention of Atrial Tachyarrythmias Related to Inter-Atrial Block By Permanent Atrial Resynchronization," Mabo et al., No. 122. For patients with this condition, a criterion for pacing is to deliver a left atrial stimulus before the natural depolarization arrives in the left atrium.

In view of the published literature, it is observed that in CHF patients improved pump function can be achieved by increasing the filling time of the left ventricle, i.e., improving the left AV delay, and specifically the left heart mechanical AV delay (MAVD); decreasing mitral valve regurgitation, (back flow of blood through the nearly closed valve) by triggering contraction of the left ventricle when and as it becomes filled; and normalizing the left ventricular activation pattern, i.e., the time sequence of left atrial contraction relative to right atrial contraction. More specifically, for a cardiac pacing system used for treating a CHF patient, the aim is to capture the left atrium; optimize the left AV delay so as to properly fill the left ventricle and provide a more normal AV delay; and activate the left ventricle as much as possible in accordance with the natural propagation path of a healthy left heart. Particularly, left ventricular timing with respect to the left atrial contraction is crucial for improving cardiac output. The mechanical closure point of the left, or mitral valve, is a crucial moment which needs to be adjusted by programming of the left AV delay. Correct programming of this variable is key for optimizing the filling of the left ventricle, and optimizing ejection fraction, or cardiac output (CO).

An observation which is important to this invention is that the exact timing of mechanical events are important for properly controlling pacing so as to optimize left ventricular output. Specifically, it is known that actual contraction of one ventricular chamber before the other has the effect of moving the septum so as to impair full contraction in the later activated chamber. Thus, while concurrent or simultaneous pacing of the left and right ventricle may achieve a significant improvement for CHF patients, it is an aim of this invention to provide for pacing of the two ventricles in such a manner that the actual mechanical contraction of the left ventricle, with the consequent closing of the valve, occurs in a desired time relationship with respect to the mechanical contraction of the right ventricle and closing of the right value. For example, if conduction paths in the left ventricle are impaired, delivering a pacing stimulus to the left ventricle at precisely the same time as to the right ventricle may nonetheless result in left ventricular contraction being slightly delayed with respect to the right ventricular contraction. As a consequence, it is important for this invention to provide a technique for measurement of mechanical events, such as a mechanical closure point of each of the ventricles, so as to be able to accurately program the sequence of pacing to achieve the desired dual ventricular pacing which optimizes ejection fraction, or cardiac output, for the individual patient.

In view of the above-noted importance of measuring mechanical events, such as mitral or tricuspid valve closure, and the importance of measuring cardiac output, it is necessary for the pacing system of this invention to employ sensors which can provide this information. It is known to use impedance sensors in pacing systems, for obtaining information concerning cardiac function. For example, reference is made to U.S. Pat. No. 5,501,702, incorporated herein by reference, which discloses making impedance measurements from different electrode combinations. In such system, a plurality of pace/sense electrodes are disposed at respective locations, and different impedance measurements are made on a time/multiplexing basis. As set forth in the referenced patent, the measurement of the impedance present between two or more sensing locations is referred to "rheography." A rheographic, or impedance measurement involves delivering a constant current pulse between two "source" electrodes, such that the current is conducted through some region of the patient's tissue, and then measuring the voltage differential between two "recording" electrodes to determine the impedance therebetween, the voltage differential arising from the conduction of the current pulse through the tissue or fluid between the two recording electrodes. The referenced patent discloses using rheography for measuring changes in the patient's thoracic cavity; respiration rate; pre-ejection interval; stroke volume; and heart tissue contractility. It is also known to use this technique of four point impedance measurements, applied thoracically, for measuring small impedance changes during the cardiac cycle, and extracting the first time derivative of the impedance change, dZ/dt. It has been found that a substantially linear relation exists between peak dZ/dt and peak cardiac ejection rate, providing the basis for obtaining a measure of cardiac output. See also U.S. Pat. No. 4,303,075, disclosing a system for measuring impedance between a pair of electrodes connected to or in proximity with the heart, and processing the variations of sensed impedance to develop a measure of stroke volume. The AV delay is then adjusted in an effort to maximize the stroke volume.

Given the demonstrated feasibility of four-chamber cardiac pacing, and the availability of techniques for sensing natural cardiac signals and mechanical events, there nonetheless remains a need for developing a system which is adapted to the cardiac condition of a patient with CHF, so as to provide pacing sequences which are tuned for improving cardiac output, and in particular for improving left heart function. It is a premise of this invention that such a system is founded upon accurate measurements of mechanical events, and use of the timing of such mechanical events to control and program pacing sequences.

SUMMARY OF THE INVENTION

It is an overall object of this invention to provide a pacing system for multiple chamber pacing, and in particular, for pacing the patient's left heart in coordination with the electrical activation and mechanical events of the patient's right heart, so as to optimize left heart output. In accordance with this invention, there is provided a four-chamber pacing system, having leads carrying electrodes positioned for pacing and sensing in or on each of the four cardiac chambers. Additionally, the leads are connected to obtain impedance measurements from which accurate timing signals are obtained reflecting mechanical actions, e.g., valve closures, so that accurate timing information is available for controlling electrical activation and resultant mechanical responses for the respective different chambers. The impedance or mechanical sensing determinations are preferably made by multiplexing through fast switching networks to obtain the desired impedance measurements in different chambers.

In a preferred embodiment, control of four-chamber pacing, and in particular left heart pacing, is based primarily upon initial detection of a spontaneous signal in the right atrium, and upon sensing of mechanical contraction of the right and left ventricles. In a heart with normal right heart function, the right mechanical AV delay is monitored to provide the timing between the initial sensing of right atrial activation (P-wave) and right ventricular mechanical contraction. The left heart is controlled to provide pacing which results in left ventricular mechanical contraction in a desired time relation to the right mechanical contraction; e.g., either simultaneous or just preceding the right mechanical contraction; cardiac output is monitored through impedance measurements, and left ventricular pacing is timed to maximize cardiac output. In patients with intra-atrial block, the left atrium is paced in advance of spontaneous depolarization, and the left AV delay is adjusted so that the mechanical contractions of the left ventricle are timed for optimized cardiac output from the left ventricle.

DESCRIPTION OF THE PREFERRED EMBODIMENTS

In the description of the preferred embodiments, and with reference to the drawings, the following designations are used:

| DRAWING DESIGNATION | DEFINITION |
|---|---|
| RA | right atrium |
| RV | right ventricle |
| RH | RA and RV |
| LH | LA and LV |
| LA | left atrium |
| LV | left ventricle |
| LAS | left atrial sense |
| RAS | right atrial sense |
| LAP | left atrial pace pulse |
| LVP | left ventricular pace pulse |
| RMAVD | time interval between RAS and mechanical contraction of RV (as measured, e.g., by valve closure) |
| LMAVD | time interval between LAS or LAP and mechanical contraction of LV |
| RAVD | time interval between RAS and QRS in RV |
| LAVD | time interval between LAS or LAP, and QRS in LV |

Figure 1:
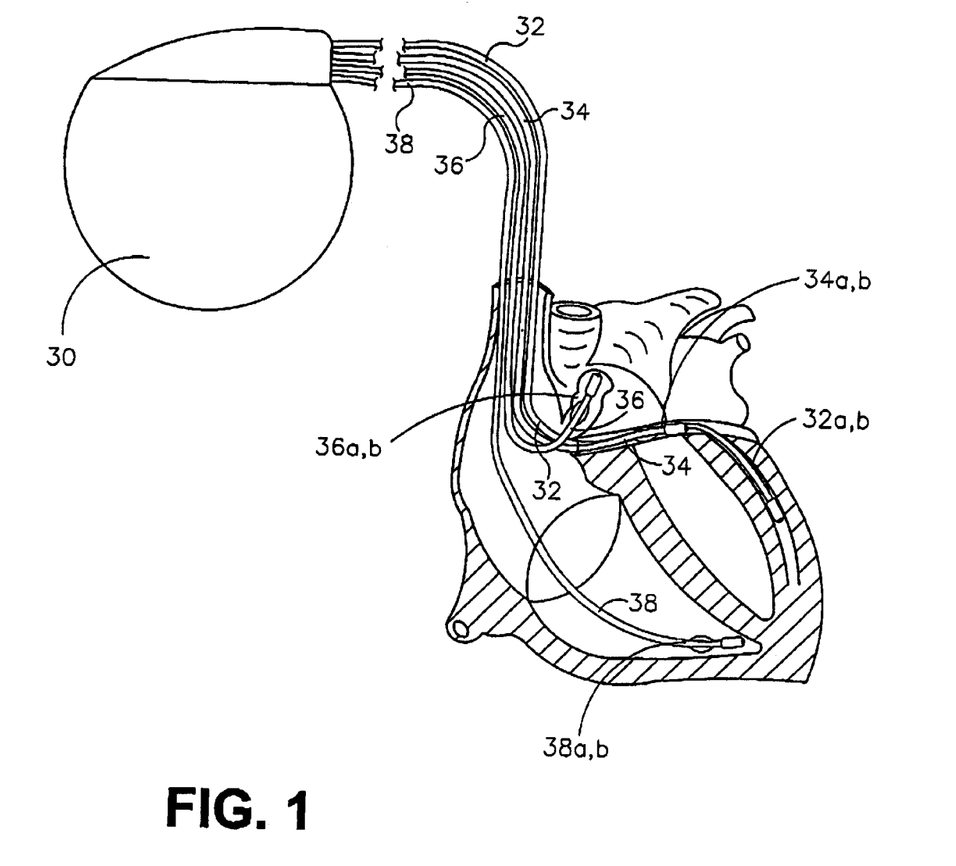
FIG. 1 is a schematic representation of a system in accordance with this invention, whereby four bipolar leads are provided, the leads being shown carrying bipolar electrodes positioned in each of the respective cardiac chambers.
Figure 2A:
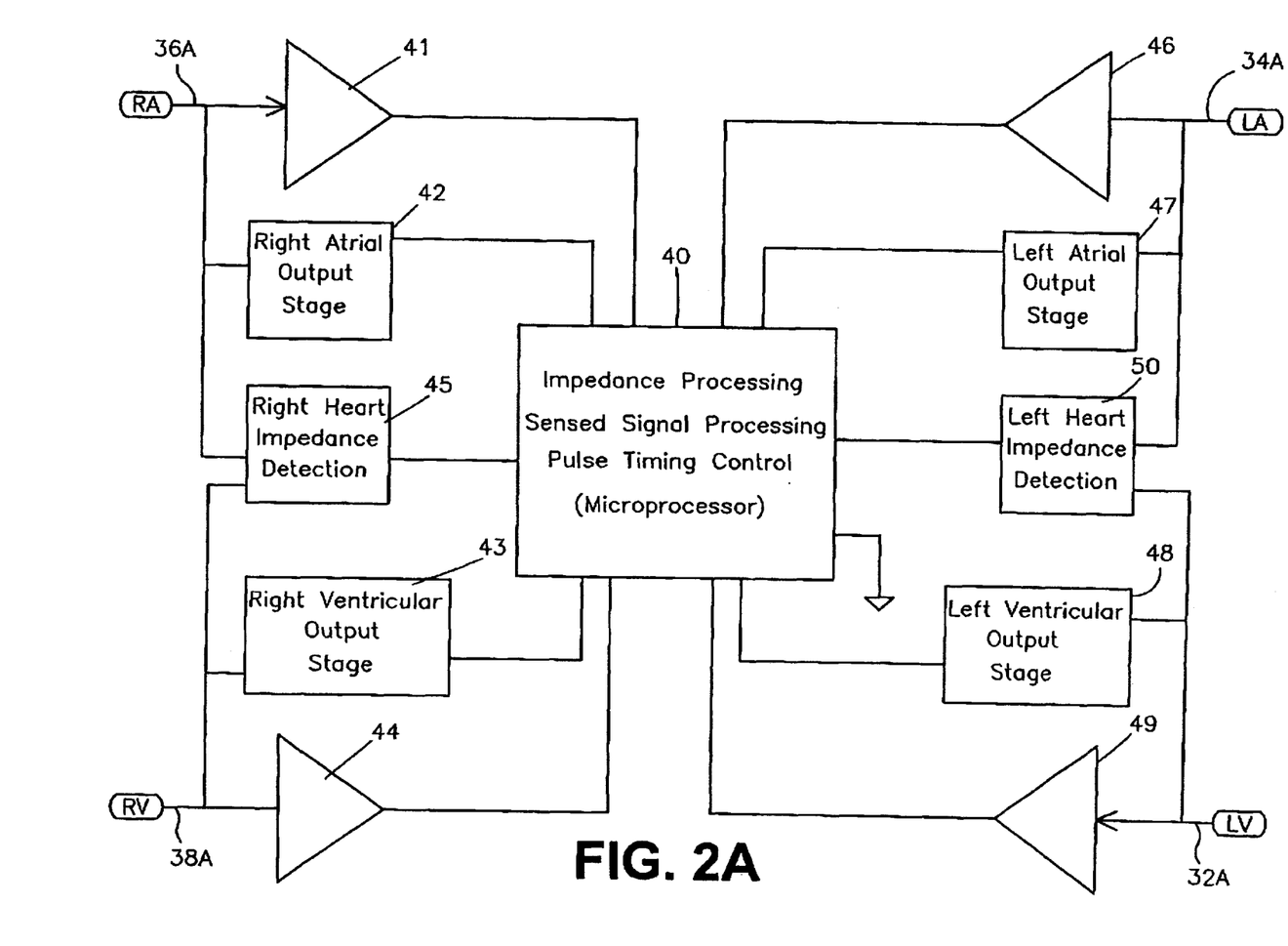
FIG. 2A is a block diagram of a four channel pacing system in accordance with this invention, for pacing and sensing in each ventricle, and for obtaining impedance signals from the left heart and the right heart.
Figure 2B:
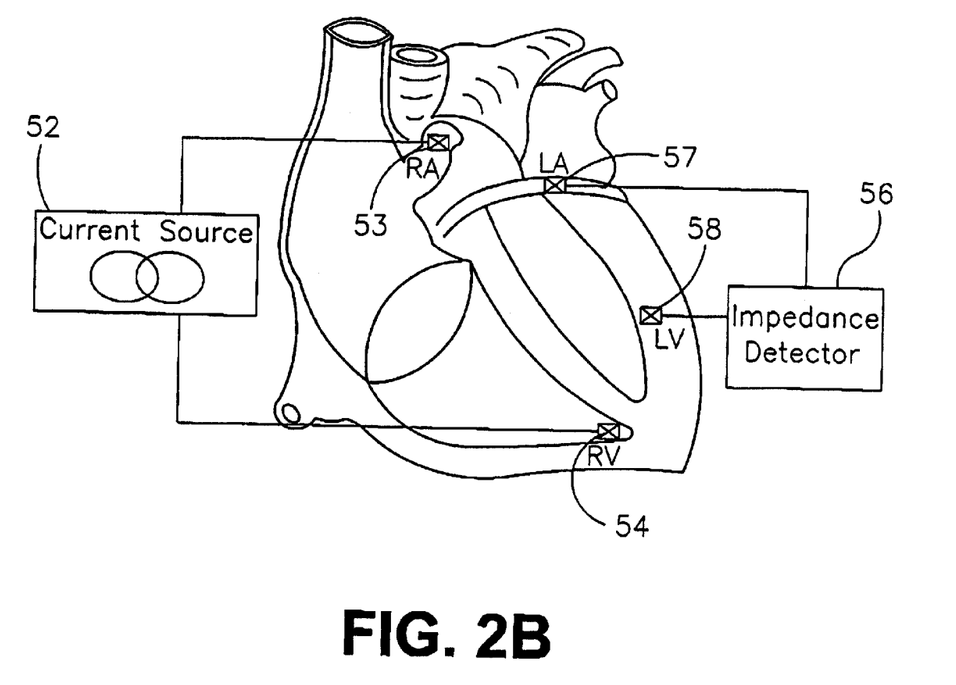
FIG. 2B is a schematic representation of an arrangement in accordance with this invention for detecting left ventricular impedance for determination of cardiac output.

Referring now to FIG. 1, there is shown a schematic representation of a four-chamber pacing system, illustrating four pacing leads providing bipolar electrodes positioned for pacing and sensing in each of the respective heart chambers, and also for impedance measurements. Pacing lead 38 is positioned conventionally such that its distal end is in the right ventricular apex position. It carries bipolar electrodes 38a and 38b adapted for pacing and sensing; additionally, these electrodes can also be used for impedance sensing as discussed below. Likewise, atrial lead 36 is positioned so that its distal end is positioned within the right atrium, with bipolar electrodes 36a, 36b. Lead 34 is passed through the right atrium, so that its distal end is positioned in the coronary sinus for pacing, sensing and impedance detection through electrodes 34a, b, as shown. Likewise, lead 32 is positioned via the coronary sinus a cardiac vein, e.g., the middle or great cardiac vein, so that distal electrodes 32a and 32b are positioned approximately as shown for pacing, sensing and impedance detection with respect to the left ventricle. The pacing leads are connected to pacemaker 30 in a conventional manner. It is to be understood that each of the four leads can have one or more additional electrodes; however, by using time multiplexing techniques as discussed below and in the referenced U.S. Pat. No. 5,501,702, pacing, sensing and impedance detection can be accomplished with only two electrodes per lead. Referring now to FIGS. 2A and 2B, there is shown a simplified block diagram of a four channel pacemaker in accordance with this invention, having the additional capability of impedance detection to sense valve movement of the left and right ventricles. Although discussion of FIG. 2A is presented with respect to valve movement, it is to be understood that the impedance detection scheme may be altered to detect other mechanical events, such as ventricular wall contraction, in a known manner.

The system of FIG. 2A contains, in the pacemaker, a central processing block 40, indicated as including timing circuitry and a microprocessor, for carrying out logical steps in analyzing received signals, determining when pace pulses should be initiated, etc., in a well known fashion. Referring to the upper left-hand corner of the block diagram, there is shown signal amplifier circuitry 41, for receiving a signal from the right atrium. Electrode 36a is illustrated as providing an input, it being understood that the second input is received either from bipolar electrode 36b, or via an indifferent electrode (the pacemaker can) in the event of unipolar sensing. Likewise, a pulse generator 42, acting under control of block 40, generates right atrial pace pulses for delivery to electrode 36a and either electrode 36b or system ground. In a similar manner, right ventricular pace pulses (RVP) are generated at output stage 43 and connected to electrode 38a, and sensed right ventricular signals are inputted to sense circuitry 44, the output of which is delivered to control block 40. Also illustrated is impedance detector 45, which receives inputs from electrodes 36a, 38a, for delivering information corresponding to right heart valve closure, which timing information is inputted into control block 40. Thus, the system enables pacing and sensing in each chamber, as well as impedance detection to provide an indication of the timing of right heart valve closure, which represents the time of mechanical contraction of the right valve.

Still referring to FIG. 2A, there are shown complementary circuit components for the left atrium and the left ventricle. Output generator stage 47, under control of block 40, delivers left atrial pace pulses (LAP) to stimulate the left atrium through electrode 34a and either electrode 34b or system ground. Inputs from the left atrial lead are connected through input circuitry 46, the output of which is connected through to control block 40. In a similar fashion, output stage 48, under control of block 40, provides left ventricular stimulus pace pulses (LVP) which are delivered across electrode 32a and either electrode 32b or system ground; and left ventricular signals are sensed from lead 32 and inputted to input circuit 49, which provides an output to block 40 indicative of left ventricular signals. Also, dual inputs from the left atrial electrode 34a and left ventricular electrode 32a are inputted into left heart impedance detector 50, which provides timing pulses to block 40 indicative of the timing of left heart (mitral) valve closure. With this arrangement, the pacemaker has the basic timing and cardiac signal information required to program delivery of pace pulses to respective heart chambers in accordance with this invention. Block 40 contains current generators for use in impedance detection; microprocessor or other logic and timing circuitry; and suitable memory for storing data and control routines.

Referring to FIG. 2B, there is shown a diagrammatic sketch of an arrangement for detecting left ventricular impedance change, which is processed in block 40 to obtain an indication of cardiac output. As shown, a current source 52 provides a constant current source across electrode 53 in the right atrium, which suitably can be electrode 36a; and right ventricular electrode 54, which suitably can be electrode 38a.

The current source can be pulsed, or it can be multiplexed in a manner as discussed below. Impedance sensors 57 and 58 provide signals representative of impedance changes therebetween, the impedance being a function of blood volume and valve closure, as discussed above. The outputs from electrodes 57, 58 is connected across impedance detector 56, which represents the microprocessor and/or other processing circuitry in block 40 for analyzing the impedance changes and making a determination of cardiac output. As is known, a measure of cardiac output can be obtained by extracting the first time derivative of cyclical impedance changes, dz/dt; a linear relationship exists between peak dz/dt and peak ejection rate.

Figure 3:
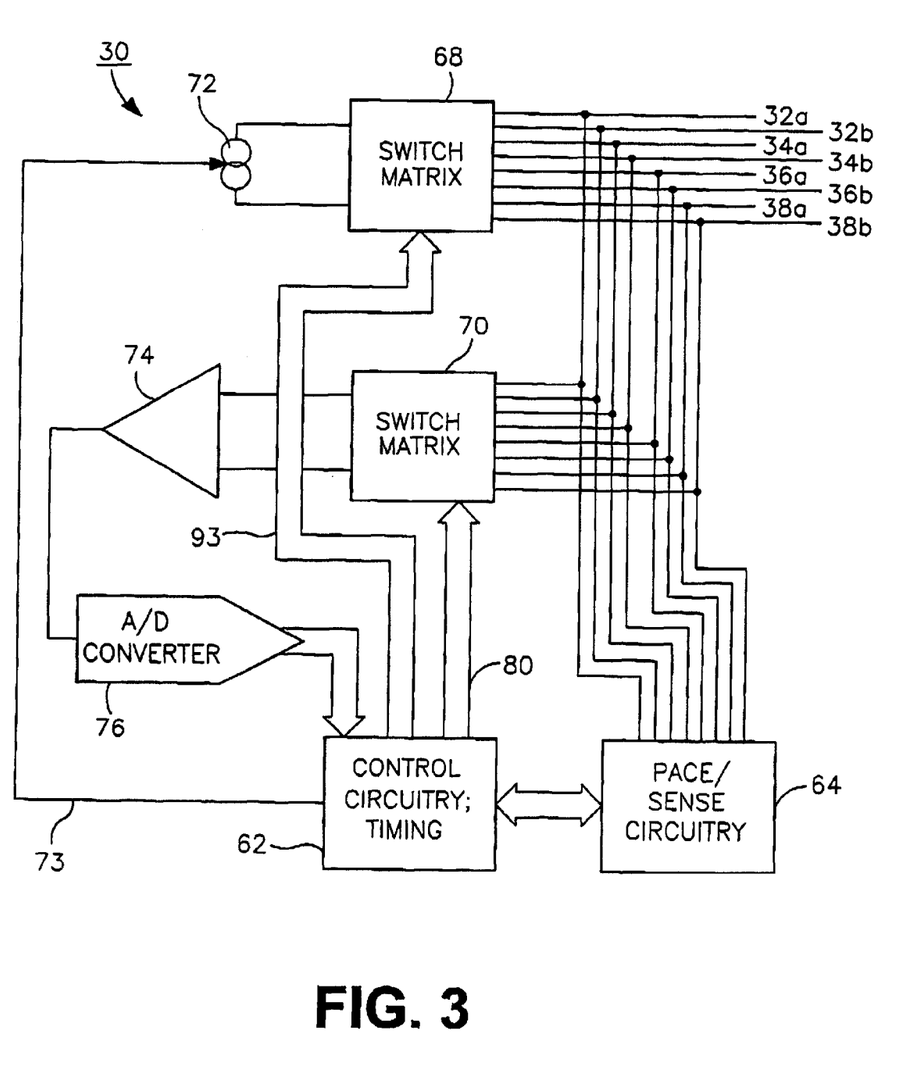
FIG. 3 is a block diagram of a four-chamber pacemaker with the ability to time multiplex impedance measurements, in accordance with this invention.

Referring now to FIG. 3, there is shown a block diagram of a pacemaker 30 in accordance with a preferred embodiment of this invention, for multiplexing connections to electrodes so as to provide for pacing and sensing in any one of the four cardiac chambers, as well as for impedance determinations between respective different lead electrodes. Reference is made U.S. Pat. No. 5,501,702, incorporated herein by reference, for a full discussion of this circuit, and in particular the multiplexing arrangement carried out by switch matrices 68, 70. The pacemaker 30 operates under control of circuitry 62, which may include a microprocessor or custom integrated circuitry, as well as associated memory, in a manner well known in the pacemaker art.

Circuitry 62 provides for processing of data, and generation of timing signals as required. Control circuitry 62 is coupled to pace/sense circuitry 64, for processing of signals indicating the detection of electrical cardiac events, e.g., P-waves, R-waves, etc. sensed from conductors which connect electrically to electrodes 32a–38b, as shown. The aforementioned leads are also coupled to a first switch matrix 68 and a second switch matrix 70. Matrix 68 establishes a selectable interconnection between specific ones of the electrodes of leads 32, 34, 36 and 38, and the current source 72, is controlled by circuit 62. In a similar manner, switch matrix 70 establishes a selectable interconnection between lead conductors corresponding to selected electrodes, and impedance detection circuit 74, for the purpose of selecting impedance measurements.

Still referring to FIG. 3, current source 72 receives control signals on line 73 from circuitry 62, and is responsive thereto for delivering constant current rheography pulses onto lead conductors selected by switching matrix 68, which in turn is switched by signals on bus 83. Impedance detection circuit 74 is adapted to monitor the voltage between a selected pair of electrodes which pair is selectably coupled by operation of switch matrix 70 which in turn is switched by signals on bus 80. In this manner, circuit 74 determines the voltage, and hence the impedance, existing between two selected electrodes. The output of circuitry 74 is connected through A/D converter 76 to control circuitry 62, for processing of the impedance signals and determination of the occurrence of mechanical events, such as left or right heart valve closure. The control of switch matrix 68 through signals on bus 78, and the control of switch matrix 70 through signals on bus 80, provides for multiplexing of different impedance signals.

It is to be understood that in the system arrangement of FIG. 3, pace/sense circuitry 64 may include separate stimulus pulse output stages for each channel, i.e., each of the four-chambers, each of which output stages is particularly adapted for generating signals of the programmed signal strength. Likewise, the sense circuitry of block 64 may contain a separate sense amplifier and processor circuitry for sensed signals from each chamber, such that sensing of respective wave portions, such as the P-wave, R-wave, T-wave, etc. from the RH and the LH, can be optimized. The pulse generator circuits and sense circuits as used herein are well known in the pacemaker art. In addition, other functions may be carried out by the control circuitry including standard pacemaker functions such as compiling of diagnostic data, mode switching, etc.

Figure 4:
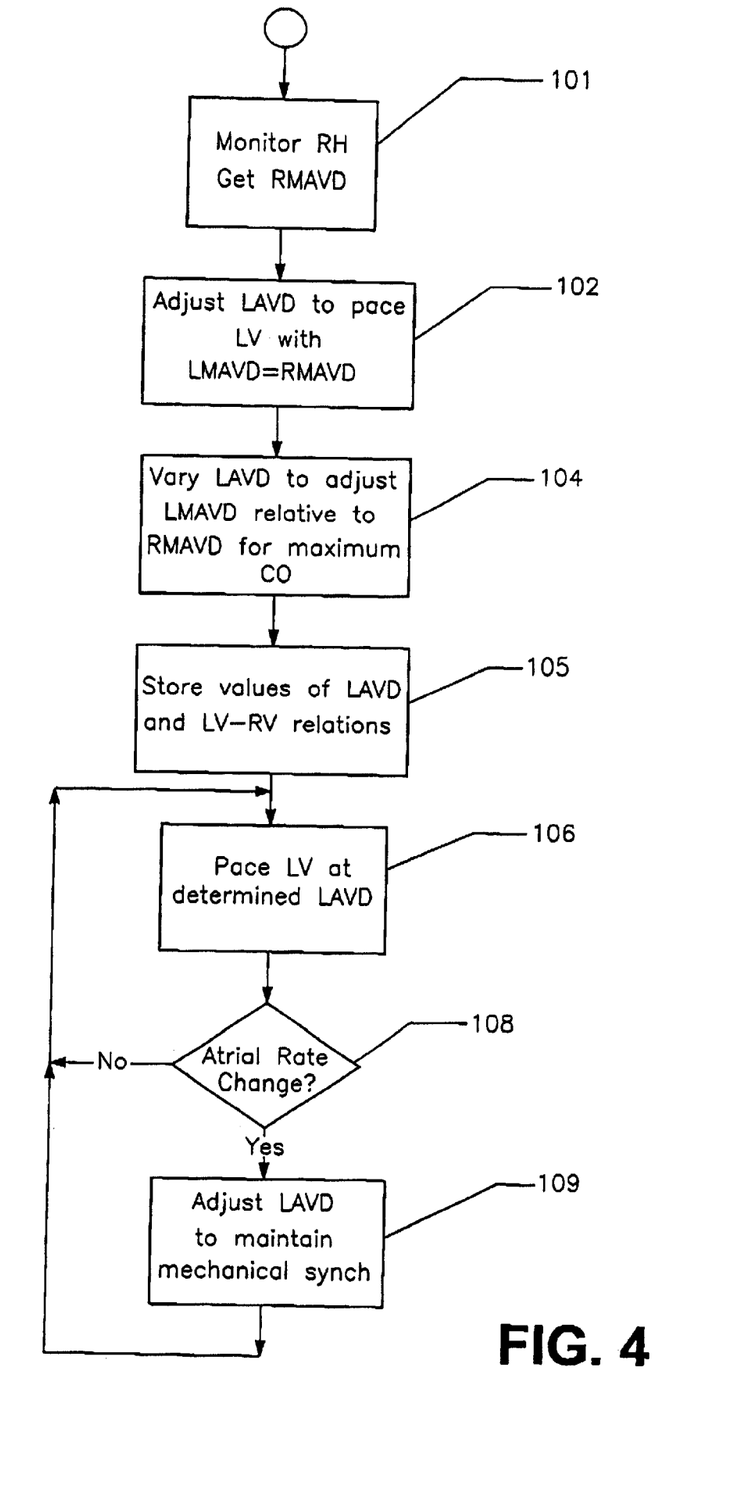
FIG. 4 is a block diagram of a system implementation in accordance with an embodiment of this invention for controlling left ventricular pacing in a patient with LBBB.

Referring now to FIG. 4, there is shown a logic control flow diagram for controlling the system of this invention to pace a patient with LBBB. The assumption is that the RH is normal, and that sinus signals from the SA node are being normally conducted to the LA; but that the LBBB is manifested by slow conduction to the LV, such that the LV does not contract when it should. As a consequence, there is mitral regurgitation, or backflow of blood through the valve because the LV does not contract when it is filled from the LA; and the contraction of the LV, when it occurs, is later than that of the RV, further contributing to decrease of LH output.

As seen at 101, the pacemaker monitors the RH, and gets a measure of RMAV. This is done by sensing right valve closure through RH impedance measurement, and timing the delay from the atrial depolarization (RAS) to valve closure.

Then, at 102, the pacemaker is controlled to pace LV with an LAVD such that LMAVD is about equal to RMAVD. During this step, impedance measurements are made in the LV, and a measure of LMAVD is obtained. Based on this determination, the value of LAVD is adjusted to substantially match LMAVD with RMAVD. Note that normal conduction through the LV takes on the order of 50-60 ms, so it is expected that the LV should be paced in advance of the occurrence of RV valve closure, so that LV valve closure occurs at about the same time as, or even a bit before RV valve closure. Causing the LV to contract just before the RV might provide an increase of LH output which outweighs the small resulting RV dysfunction due to the septum being pulled toward the LV first. Thus, the timing of delivery of each LVP is adjusted to set LMAVD approximately equal to RMAVD. Then, at 104, the value of LAVD is further adjusted, while R and L valve closure is monitored, and LMAVD is adjusted relative to RMAVD. This adjustment, or variation of LMAVD, may be made by incrementally changing LAVD each cycle, or each n cycles, to scan relative to the value of RMAVD. Cardiac output is obtained through a left heart impedance measurement, and appropriate signal processing, for each setting of the differential between the right and left valve closures, and respective values of CO and LMAVD are stored at 105. The highest, or maximum value of cardiac output is determined, and LAVD is set so that the resultant MLAVD is at the differential compared to RMAVD to yield the highest cardiac output. In this manner, the timing of left ventricular pace pulses is set to produce substantial biventricular mechanical synchronization for the greatest cardiac output. The determined value of LAVD and the corresponding LV-RV difference is stored.

Still referring to FIG. 4, at 106 the pacemaker proceeds to pace the LV with this established value of LAVD, providing mechanical synchronization. Of course, if the natural sinus rate varies, the pacemaker wants to follow; if the spontaneous RAVD varies, but the LAVD doesn't follow the change, the mechanical synchronization will be lost. Accordingly, at 107 the pacer monitors the natural sinus rate, or atrial pacing rate, and determines if there has been a significant change in atrial rate. If yes, at 109, the pacer adjusts LAVD accordingly to maintain mechanical sync for optimum output. Although not shown, the pacemaker can periodically go back to block 101 to redetermine the desired value of LAVD.

Figure 5:
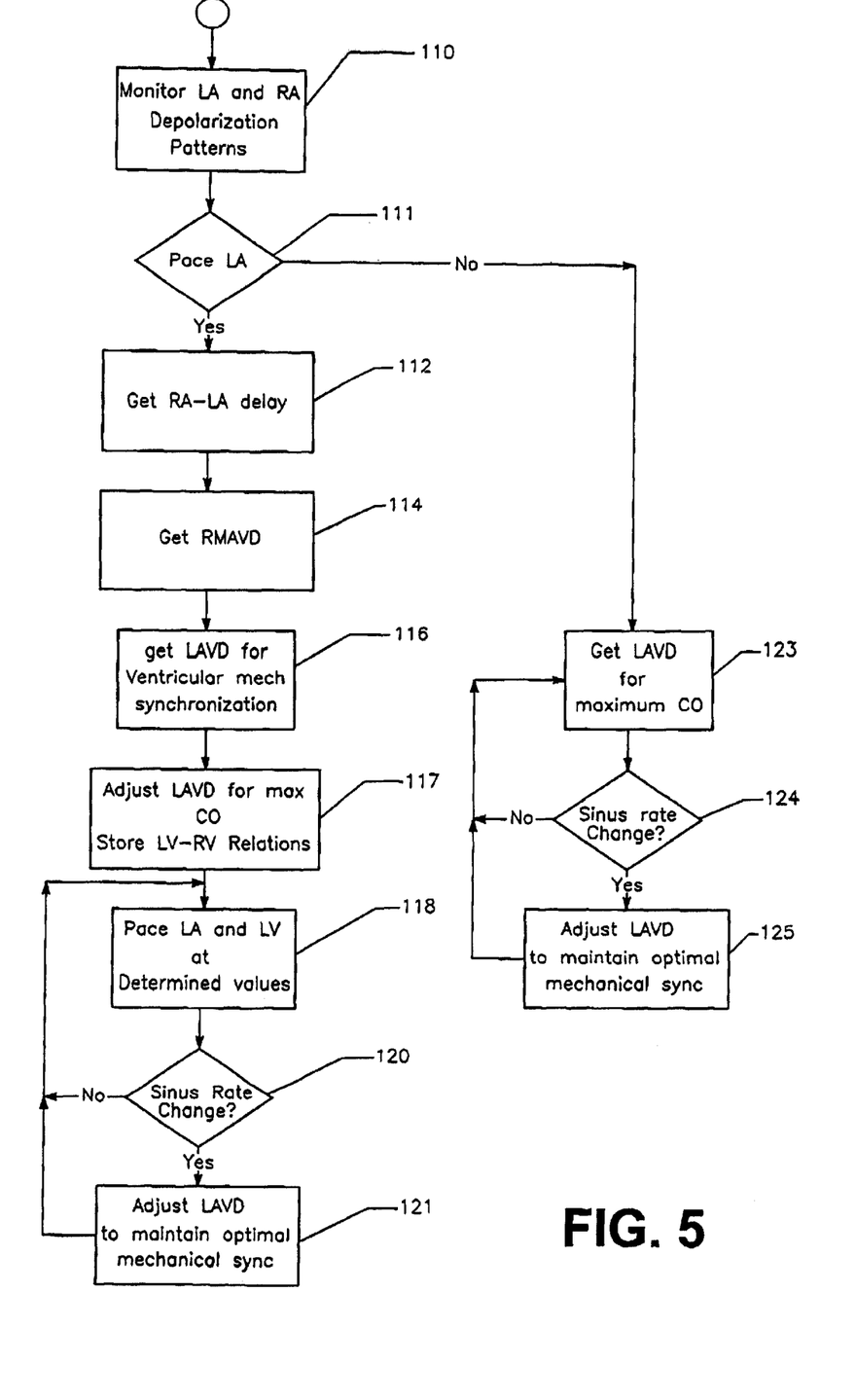
FIG. 5 is a flow diagram for a system implementation in accordance with an embodiment of this invention, for controlling left atrial and ventricular pacing in a patient with IAB.

Referring now to FIG. 5, there is shown a flow diagram for pacing of a patient with IAB; such patient may have LBBB as well. Here, it is necessary to take control of the LA by pacing before atrial depolarization is conducted (late) to the LA. At 110, the pacemaker monitors the pattern of LA depolarization relative to RA depolarization, i.e., it determines the inter-atrial delay. At 111, it is determined whether the LA should be paced, based on the atrial depolarization pattern. If yes, the pacemaker sets an RA-LA delay at 112, which corresponds to a healthy heart, and which enables capture of the LA. At 114, the value of RMAVD is obtained, as was described in connection with FIG. 4. Then, at 116, LAVD is determined for a first setting of mechanical sync; this can be done by setting LAVD to produce LV contraction at the same time as RV contraction (valve closure), or earlier by a small time increment. Then, LAVD is varied, as shown at 117, and LMAVD and CO are determined corresponding to each value of LAVD. The value of LAVD is set to that value which corresponds to maximum cardiac output, and this value and the LV-RV mechanical relation, or mechanical sync value is stored for the chosen LAVD. At 118, the pacemaker paces LA and LV, in accord with the values that have been determined. In the event of significant change in atrial rate, LAVD is adjusted to compensate for the rate change, and to substantially maintain the LV-RV mechanical relationship previously found to correspond to maximum cardiac output, as shown at 120, 121. Although not shown, in the event of large changes in the sinus rate, or passage of a predetermined amount of time, determination of inter-atrial delay and LAVD can be repeated automatically.

Figure 6:
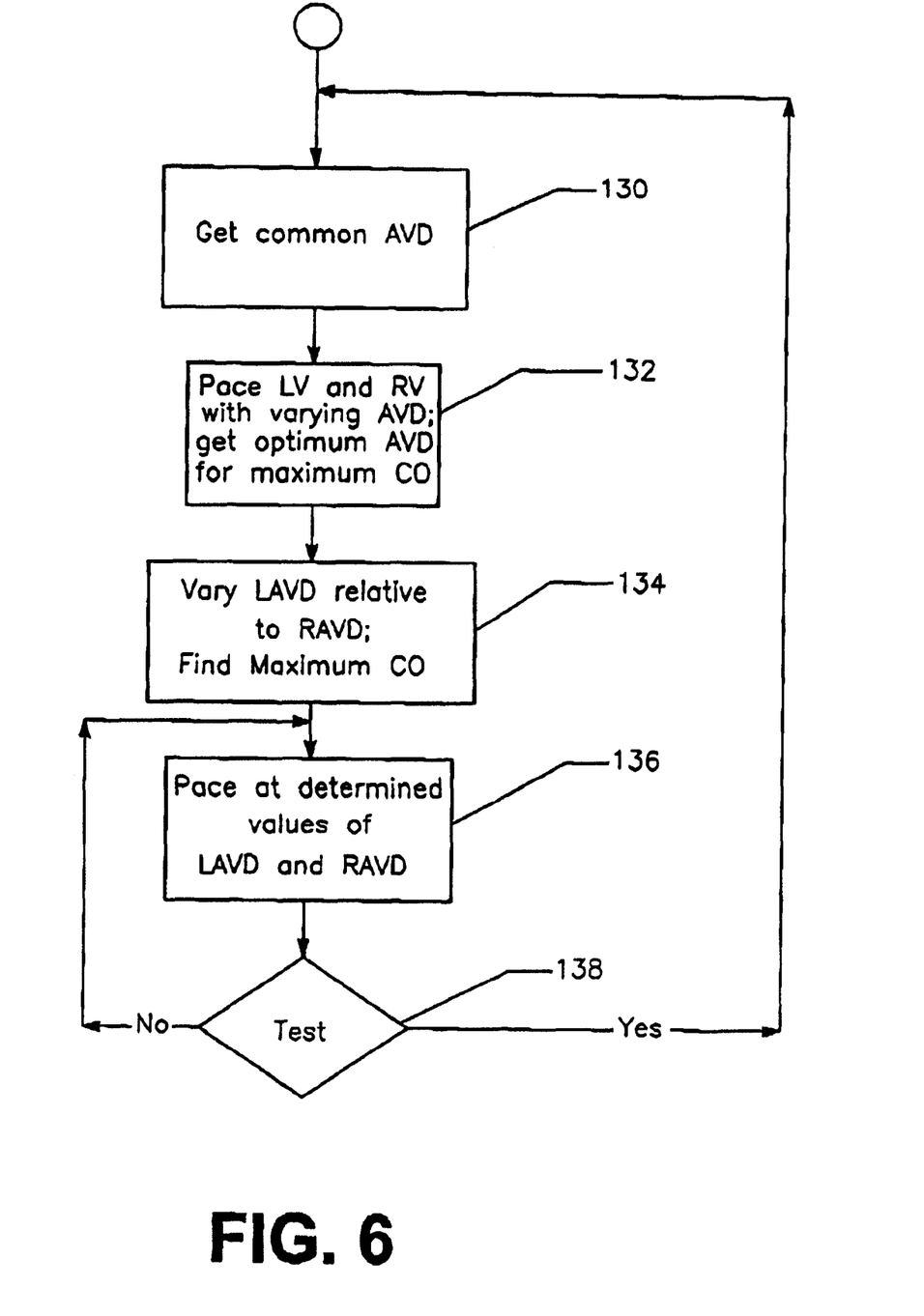
FIG. 6 is a flow diagram of a routine in accordance with this invention for optimizing bi-ventricular pacing to provide maximum cardiac output.

Referring now to FIG. 6, there is shown a simplified flow diagram for a procedure in accordance with this invention for carrying out bi-ventricular pacing so as to maximize cardiac output (CO). This routine is adapted for patients who need right ventricular pacing, and who can benefit from synchronous left ventricular pacing as well. In this example, it is assumed that atrial pacing is not required, but if the patient requires atrial pacing, the routine can be adapted appropriately.

At block 130, a common value of AV delay (AVD) is first set. At block 132, both the left ventricle and the right ventricle are paced, initially with the previously set value of AVD, but then with a varying AVD. As AVD is varied, or scanned relative to the initial setting, the pacemaker makes determinations of cardiac output by processing impedance signals from the left heart, or left ventricle, in the manner discussed above. Values of CO are stored together with the different values of AVD, and the optimum value of a common AVD is determined corresponding to maximum CO. Then, at block 134, the value of LAVD is varied relative to RAVD, such that the left pacing pulse is delivered at differing times from the right pacing pulse. It is to be remembered, as discussed above, that for maximum cardiac output, it may be desirable to pace the left ventricle shortly before the right ventricle, and this step is a searching step to determine the time relationship between the two ventricular pace pulses which results in the best cardiac output. CO is determined as the ventricular sync relationship is varied, and the corresponding optimum LAVD is determined. When this has been obtained, the routine goes to block 136 and paces the patient at the determined values of LAVD and RAVD. Periodically, as indicated at 138, the pacemaker can determine whether a test is desired. If yes, the routine branches back to 130, to loop through the test and redetermine the optimum values of LAVD and RAVD. It is to be noted that the steps of blocks 132 and 134 can be done in a reverse sequence, i.e., step 134 first and then step 132.

Figure 7:
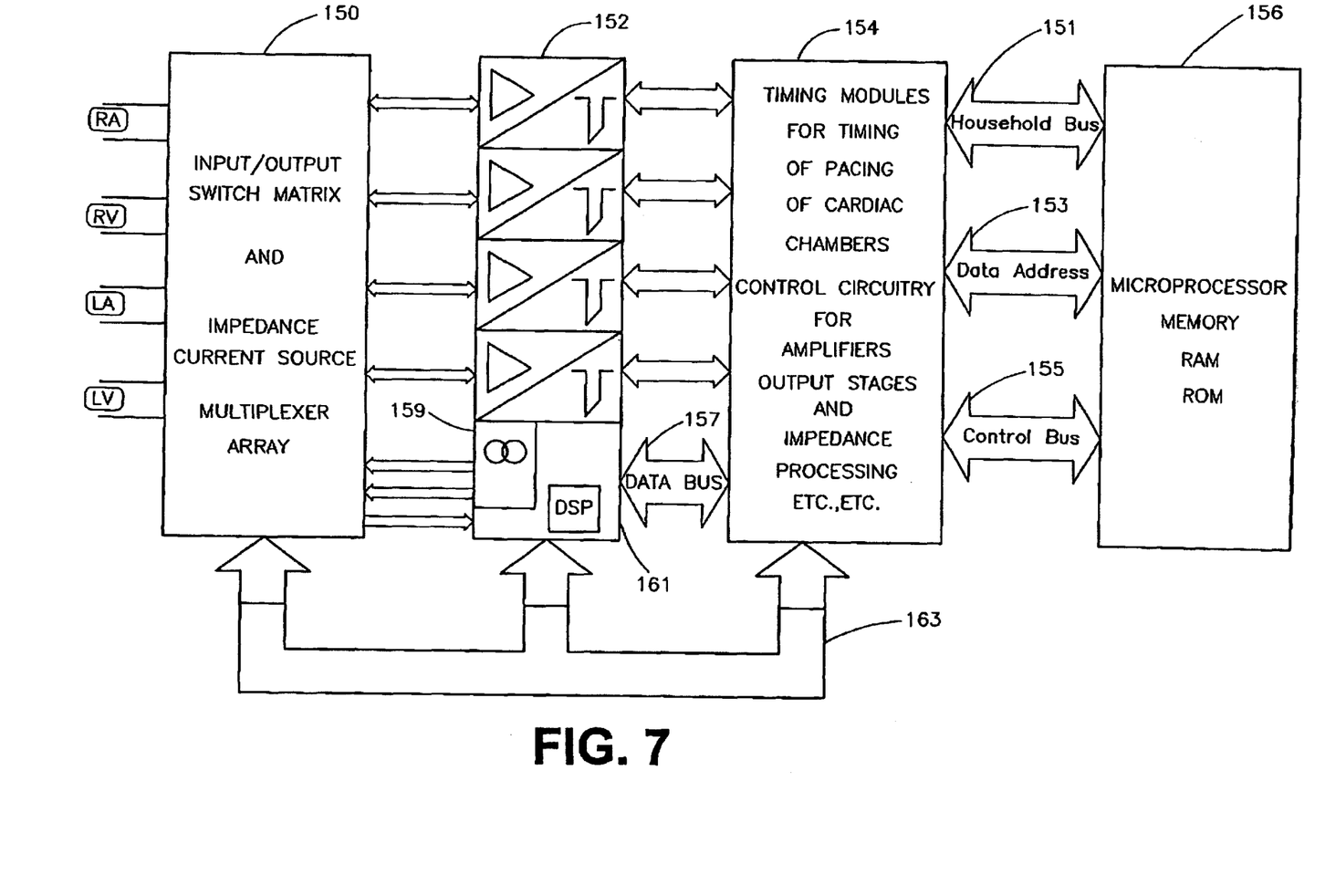
FIG. 7 is a block schematic of a pacemaker in accordance with this invention for providing selectable four-chamber pacing and cardiac signal sensing, as well as impedance sensing between selected combinations of the four heart chambers.

Referring now to FIG. 7, there is shown an alternate block diagram of component portions of a pacemaker in accordance with this invention, for providing maximum flexibility in terms of pacing, cardiac signal sensing and impedance sensing. At least two electrodes are positioned in or proximate to each heart chamber, in the manner as discussed above in connection with FIG. 1, and connected in turn to block 150. As indicated in FIG. 7, block 150 is an output/input switch matrix, and interconnects with block 152 in the manner as described in FIG. 3. Thus, block 152 provides pacing pulses which can be connected through matrix 150 to each of the four chambers, and has sense amplifier circuitry for sensing signals from each of the four chambers. Block 150 further provides a multiplex switch array for switching a current source across selected pairs of the eight electrodes for impedance measuring purposes, again in accordance with the discussion of FIG. 3. The sensed impedance signals are suitably transferred from array 150 to digital signal processing circuitry 161, which is part of block 152. Block 152 is in two-way connection with the timing modules shown in block 154, for timing generation of pace pulses, current source pulses, and the generation of sensing windows. Blocks 150, 152 and 154 are further inter-connected by control bus 163. Data is transferred between signal processing block 170 and block 154 across data bus 157. Block 154 in turn is inter-connected with microprocessor 156, through household bus 151, data bus 153 and control bus 154. By this arrangement, impedance sensing can be carried out across any combination of the four heart chambers, e.g., right atrium vs. left atrium; right ventricle vs. left ventricle; right atrium vs. left ventricle; and left atrium vs. right ventricle. Impedance measurements between these combinations of chambers can be carried out in accordance with this invention, for purposes of analyzing and confirming arrhythmias, including fibrillation. Further, changes in conduction patterns, as seen in the morphology of such impedance measurements, can be monitored and processed for making determinations of progression of heart failure. Thus, cross-measurements of RA-LV and LA-RV can be useful in obtaining histories to determine changes indicating progression of heart failure.

Figure 8A:
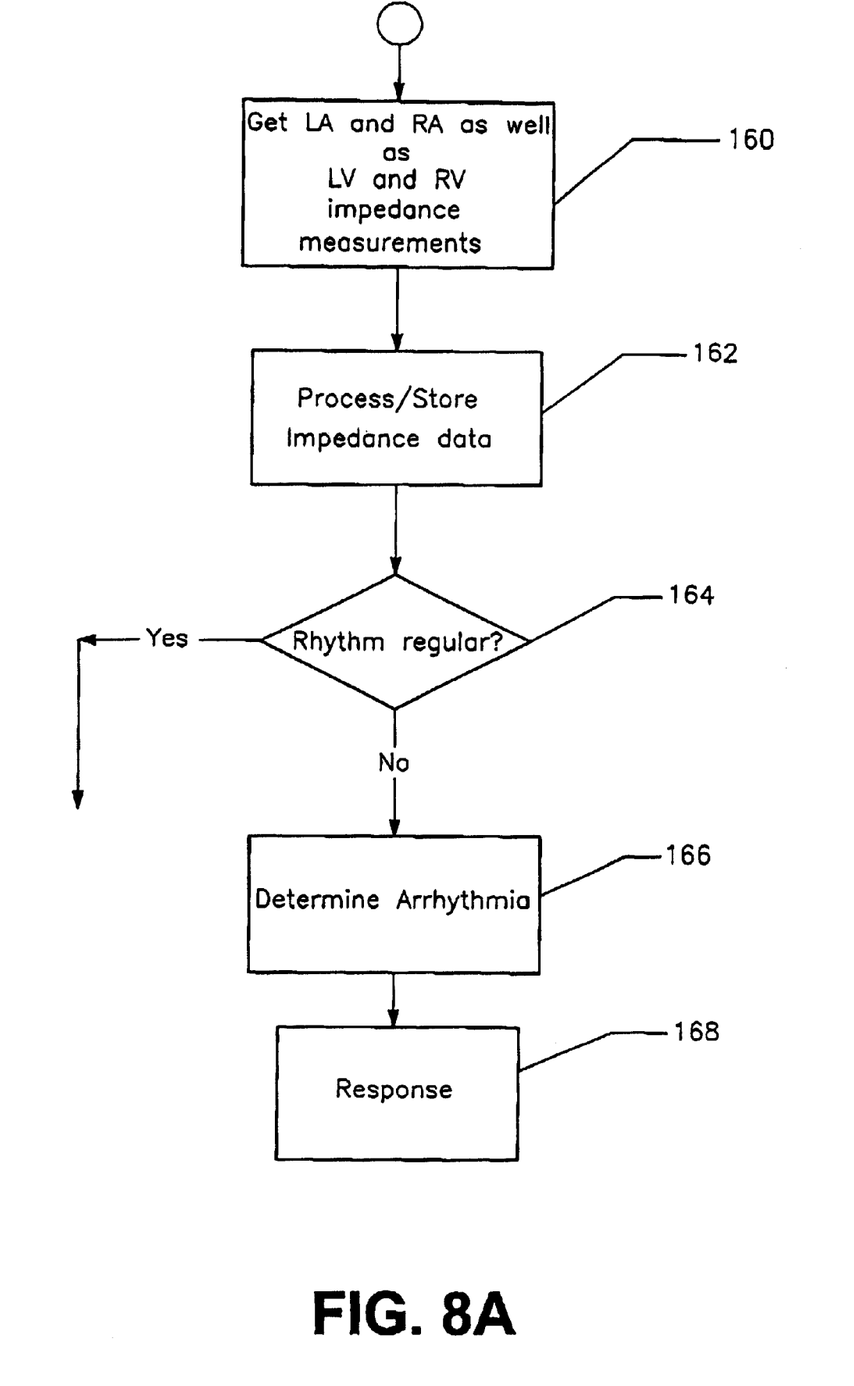
FIG. 8A is a flow diagram of a process using inter-atrial or interventricular impedance measurements for determination of existence of arrhythmias.
Figure 8B:
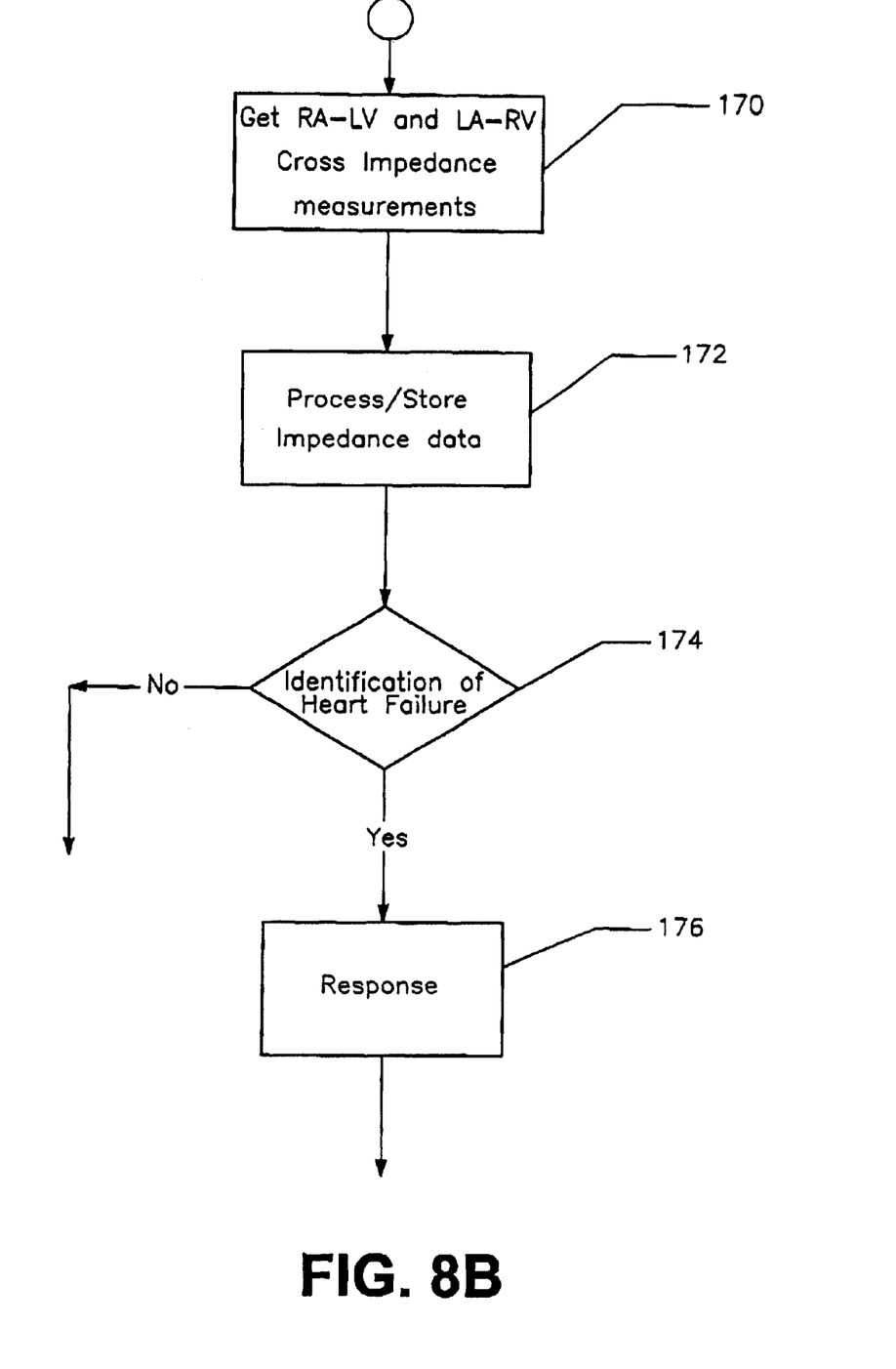
FIG. 8B is a flow diagram illustrating a procedure for obtaining atrio-ventricular cross-impedance measurements for obtaining indications of heart failure.

Referring now to FIG. 8A, at block 160, the pacemaker first obtains impedance measurements either between LA and RA, or between LV and RV. These impedance values are processed at 162, and at 164 a determination is made as to whether the atrial or ventricular rhythms are regular or non-physiological. This determination can be made, for example, simply by sensing differences over time and comparing such differences to predetermined criteria. If a rhythm is determined not to be regular, then a determination of arrhythmia is made at 166. A suitable response is made at 168. Referring to FIG. 8B, at block 170 the pacemaker obtains cross-measurements of impedances, e.g., between RA and LV or between LA and RV. These measurements are stored and processed as indicated at 172, and evaluated at 174 to determined whether they indicate HF or progression toward HF. If yes, an appropriate response can be made, illustrated at 176, e.g., providing a warning which can be retrieved by an external programmer.

The scope of the invention extends to other conditions of CHF, in addition to the ones illustrated here. In each case, the condition of the patient must be responded to on an individual basis. However, in accordance with this invention, the system response includes a determination of mechanical events, e.g., valve closure, preferably in each side of the heart, and programming of pacing escape intervals based on consideration of the mechanical events and a determination of variations of cardiac output with variations of LAVD and/or mechanical ventricular synchronization. The system of this invention can be used in an implanted pacemaker system; or, the system procedures can be carried out with an external system, for determination of optimum programming of a pacemaker which is to be implanted or re-programmed.

What is claimed is:

1. A pacing system for pacing a left side of a patient's heart, comprising:

first means for obtaining indications of mechanical contractions of the right ventricle, said first means comprising an impedance measuring circuit for obtaining an impedance signal representative of impedance and processing means for processing said impedance signal;

left ventricular pacing means or pacing the left ventricle; and

LV control means for controlling the timing of said left ventricular pacing relative to indicated right ventricular mechanical contractions, comprising left atrial pacing means for pacing the patient's left atrium, left AV control means for controlling the left AV delay between pacing the left-atrium and the left ventricle, cardiac output means for measuring left heart output as a function of said left AV delay, wherein said left AV control means further comprises maximizing means for adjusting said left AV delay to maximize left cardiac output;

LA means for determining the timing of left atrial depolarization;

CO means for measuring cardiac output from the patient's left heart;

wherein said control sync means further comprises LAVD means for controlling said pacing means to deliver pacing pulses to said patient's left ventricle at a left atrio-ventricular delay following left atrial depolarizations, and adjusting means for adjusting said left atrio-ventricular delay to correspond to maximum measured cardiac output.

2. A four chamber cardiac pacing system for pacing a patient's heart, the heart having four chambers, the system comprising:

an implantable cardiac stimulator comprising an hermetically sealed housing and disposed therewithin means for delivering cardiac pacing pulses. means for sensing cardiac depolarizations, and means for determining impedance between electrodes positioned within the heart, and a plurality of cardiac pacing leads operably connected to the cardiac stimulator, each lead comprising at least one stimulation or sensing electrode the pacing leads being suitable for positioning in separate ones of the heart's chambers;

wherein the means for determining measuring impedance further comprises;

impedance means for obtaining impedance measurements between a predetermined pair of the electrodes;

processing means for processing said impedance measurements and determining changes in said measurements over a period of time, and means for determining whether any of said changes occurs which indicates a physically abnormal heart condition.

3. The system described in claim 2, wherein said change determining means determines whether any such changes occur which are indicative of arrhythmia.

4. The system described in claim 2, wherein said change determining means further comprises means for determining whether said any such changes occur which indicate a heart failure condition.

5. The system described in claim 2, wherein the impedance determining means further comprises programmable selection means for selecting impedance measurements between any two of said four heart chambers.

* * * * *

UNITED STATES PATENT AND TRADEMARK OFFICE
CERTIFICATE OF CORRECTION

PATENT NO.     : 6,223,082 B1
DATED          : April 24, 2001
INVENTOR(S)    : Bakels et al.

It is certified that error appears in the above-identified patent and that said Letters Patent is hereby corrected as shown below:

Column 11,
Line 24, change "left-atrium" to -- left atrium --.

Column 12,
Line 14, change "electrode" to -- electrode, --.

Signed and Sealed this

Eighteenth Day of March, 2003

JAMES E. ROGAN
*Director of the United States Patent and Trademark Office*